US006432423B1

(12) United States Patent
Maignan et al.

(10) Patent No.: US 6,432,423 B1
(45) Date of Patent: Aug. 13, 2002

(54) USE OF HYPERBRANCHED POLYMERS AND DENDRIMERS COMPRISING A PARTICULAR GROUP AS FILM-FORMING AGENT, FILM-FORMING COMPOSITIONS COMPRISING SAME AND USE PARTICULARLY IN COSMETICS AND PHARMACEUTICS

(75) Inventors: Jean Maignan, Tremblay en France; Sylvie Genard, Paris, both of (FR)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 09/581,752

(22) PCT Filed: Nov. 26, 1998

(86) PCT No.: PCT/FR98/02537

§ 371 (c)(1),
(2), (4) Date: Jun. 23, 2000

(87) PCT Pub. No.: WO99/32076

PCT Pub. Date: Jul. 1, 1999

(30) Foreign Application Priority Data

Dec. 19, 1997 (FR) ............................................. 97 16175

(51) Int. Cl.$^7$ ............................ A61K 6/00; A61K 7/04; A61K 31/74; A61K 47/48
(52) U.S. Cl. ...................... 424/401; 424/61; 424/78.02; 424/78.17; 424/DIG. 16
(58) Field of Search ............................... 424/401, 78.02, 424/61, 78.17, DIG. 16

(56) References Cited

U.S. PATENT DOCUMENTS

| | | | | |
|---|---|---|---|---|
| 5,362,478 A | * | 11/1994 | Desai et al. ................... 424/9 |
| 5,627,045 A | * | 5/1997 | Bochner et al. ............... 435/34 |
| 6,020,457 A | * | 2/2000 | Klimash et al. ............. 528/373 |
| 6,068,835 A | * | 5/2000 | Franzke et al. .......... 424/70.11 |

FOREIGN PATENT DOCUMENTS

| | | |
|---|---|---|
| DE | 1 595 016 | 3/1970 |
| EP | 0 582 152 | * 2/1994 |
| EP | 0 736 297 | * 10/1996 |
| FR | 2 761 691 | 10/1998 |
| WO | WO 97/14404 | 4/1997 |
| WO | WO-98/44024 | * 10/1998 |

OTHER PUBLICATIONS

Toru Takagishi et al., "Macromolecule–Small Molecule Interactions; Introduction of Additional Binding Sites in Polyethyleneimine by Disulfide Cross–linkages", Biopolymers, vol. 11, No. 2, 1972, pp. 483–491.

English language Derwent Abstract of DE 1 595 016, Mar. 1970.

English language Derwent Abstract of FR 2 761 691, Oct. 1998.

* cited by examiner

Primary Examiner—Michael G. Hartley
Assistant Examiner—Michael A. Willis
(74) Attorney, Agent, or Firm—Finnegan, Henderson, Farabow, Garrett & Dunner, LLP

(57) ABSTRACT

The invention concerns the use of hyperbranched polymers and dendrimers, comprising at least one group of formula (I) in which: Y represents the oxygen atom or a NH group: and A represents a $C_1$–$C_{12}$ alkane di-yl group, linear, branched or cyclic, saturated or unsaturated; said group being optionally interrupted by one or several heteroatoms and/or substituted by a function selected among: amino (—$NH_2$): acylamino (—NH—CO—R) in which R represents a $C_1$–$C_{10}$ alkyl group, linear, branched or cyclic, saturated or unsaturated; carboxylic acid (—COOH), ester (—COOR) in which R represents a $C_1$–$C_{10}$ alkyl group, linear, branched or cyclic, saturated or unsaturated, as film-forming agent. The invention also concerns a film-forming composition comprising said compound and its use particularly in cosmetics or pharmaceutics.

36 Claims, No Drawings

USE OF HYPERBRANCHED POLYMERS AND DENDRIMERS COMPRISING A PARTICULAR GROUP AS FILM-FORMING AGENT, FILM-FORMING COMPOSITIONS COMPRISING SAME AND USE PARTICULARLY IN COSMETICS AND PHARMACEUTICS

This application is a 371 of PCT/FR98/02537, filed Nov. 26, 1998.

The present invention relates to the use of novel compounds which make it possible in particular to obtain films on a substrate, and to their application in particular in cosmetics or in pharmaceuticals.

Hyperbranched polymers and dendrimers are well known in the prior art. Hyperbranched polymers are molecular constructions having a branched structure, generally around a core. Their structure generally lacks symmetry, the base units or monomers used to construct the hyperbranched polymer can be of diverse nature and their distribution is non-uniform. The branches of the polymer can be of different natures and lengths. The number of base units, or monomers, may be different depending on the different branching. While at the same time being asymmetrical, hyperbranched polymers can have: an extremely branched structure, around a core; successive generations or layers of branching; a layer of end chains.

Hyperbranched polymers are generally derived from the polycondensation of one or more monomers ABx, A and B being reactive groups capable of reacting together, x being an integer greater than or equal to 2, but other preparation processes may be envisaged. Hyperbranched polymers are characterized by their degree of polymerization DP=1-b, b being the percentage of non-terminal functionalities in B which have not reacted with a group A. Since the condensation is not systematic, in contrast with the synthesis of dendrimers, the degree of polymerization is less than 100%. An end group T can be reacted with the hyper-branched polymer to obtain a particular functionality on the ends of chains.

Several hyperbranched polymers can be combined together, via a covalent bond or another type of bonding, by means of their end groups. Such polymers, known as bridged polymers, fall within the definition of the hyperbranched polymers according to the present invention.

Dendrimers are highly branched polymers and oligomers having a well-defined chemical structure. As a general rule, dendrimers comprise a core, a given number of generations of branches, or spindles, and end groups. The generations of spindles consist of structural units which are identical for the same generation of spindles and which may be identical or different for different generations of spindles. The generations of spindles extend radially in a geometrical progression from the core. The end groups of a dendrimer from the Nth generation are the end functional groups of the spindles of the Nth generation or end generation.

The definition of dendrimers given above includes molecules containing symmetrical branching; it also includes molecules containing non-symmetrical branching, such as, for example, dendrimers whose spindles are lysine groups, in which the branching of one generation of spindles on the preceding generation takes place on the α and ε amines of lysine, which leads to a difference in the lengths of the spindles of different branching.

Dense star polymers, starburst polymers and rod-shaped dendrimers are included in the present definition of dendrimers. The molecules known as arborols and cascade molecules also fall within the definition of dendrimers according to the present invention.

Several dendrimers can be combined together, via a covalent bond or another type of bonding, by means of their end groups to give species known as bridged dendrimers or dendrimer aggregates. Such species are included in the definition of dendrimers according to the present invention.

Dendrimers can be in the form of an assembly of molecules of the same generation, which are referred to as monodisperse assemblies; they can also be in the form of assemblies of different generations, known as polydisperse assemblies. The definition of dendrimers according to the present invention includes both monodisperse and polydisperse assemblies of dendrimers.

French patent application FR 97/04085 in the name of the Applicant in particular discloses novel polymers chosen from hyperbranched polymers and dendrimers, comprising functional groups corresponding to the following formula:

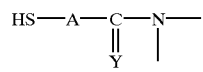

in which
Y represents an oxygen atom or an NH group,
A represents a linear, branched or cyclic, saturated or unsaturated $C_1$–$C_{12}$ alkanediyl group, this group optionally being interrupted with one or more hetero atoms and/or substituted with a function chosen from amino, acylamino, carboxylic acid and ester.

These polymers find an application in particular in cosmetics and dermatology as antioxidants or reducing agents.

Now, the Applicant has found, surprisingly, that the said polymers can also be used to allow the preparation of compositions, in particular cosmetic or pharmaceutical compositions, which make it possible to obtain a film when they are deposited on a substrate.

Thus, a subject of the present invention is the use of at least one compound chosen from hyperbranched polymers and dendrimers, comprising at least one group of formula:

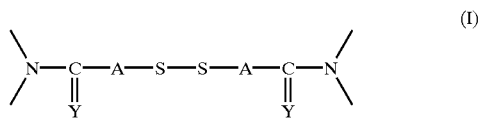

(I)

in which:
Y represents an oxygen atom or an NH group, and
A represents a linear, branched or cyclic, saturated or unsaturated $C_1$–$C_{12}$ alkanediyl group, this group optionally being interrupted with one or more hetero atoms and/or substituted with a function chosen from:
amino (—$NH_2$),
acylamino (—NH—CO—R) in which R represents a linear, branched or cyclic, saturated or unsaturated $C_1$–$C_{10}$ alkyl group,
carboxylic acid (—COOH),
ester (—COOR) in which R represents a linear, branched or cyclic, saturated or unsaturated $C_1$–$C_{10}$ alkyl group, as film-forming agent.

Another subject of the invention is a film-forming composition comprising at least one compound chosen from hyperbranched polymers and dendrimers, comprising at least one group of formula (I), the said composition being able to be obtained by oxidation of a composition comprising at least one polymer chosen from hyperbranched polymers and dendrimers comprising at least one group of formula (II).

Another subject of the invention is the use of at least one polymer chosen from hyperbranched polymers and dendrimers comprising at least one group of formula (II), for the preparation of a film-forming composition comprising at least one compound chosen from hyperbranched polymers and dendrimers comprising at least one group of formula (I), or of a composition as defined above.

Another subject of the invention is a process for obtaining a film on a support, in which a composition as defined above is applied to the said support.

Another subject of the invention is a process for obtaining a film on a support, in which a composition comprising a polymer is applied to the said support, this polymer being chosen from hyperbranched polymers and dendrimers comprising at least one group of formula (II), and the said composition is oxidized during or after its application to the said support.

The prior art discloses a certain number of film-forming agents for obtaining films. In particular, mention may be made of film-forming polymers which may be radical-mediated polymers or polycondensates, among which mention may be made of acrylic polymers and polyurethanes. Such polymers are used in particular in the field of hair care, for example in lacquers, or in the field of make-up, for example in mascaras or nail varnishes in an organic solvent medium.

However, these film-forming agents have certain drawbacks. In particular, these film-forming agents form films as soon as they are deposited on the support.

In contrast, the compounds according to the invention form films only in oxidizing medium. Thus, it is possible to apply an aqueous or aqueous-alcoholic solution, for example, of thiols (II) as a thin layer on a support, and then, at the time chosen, to chemically oxidize or to allow to oxidize freely, in particular in open air, the said thiols into compounds (I), which compounds will form, on drying, on the support, a highly adherent and water-washable film.

The compounds according to the invention allow the production of films similar to those obtained with film-forming polymers of the prior art.

Depending on the oxidation conditions, the quality of the films obtained can vary: tacky or non-tacky films, glossy or matt films, etc.

Thus, as a function of the oxidation conditions, glossy films can readily be obtained, which adhere well to the support and are non-tacky; when such films comprise a pigment or a dye, they do not mark the support on which they are deposited since they do not bleed.

The compounds which can be used within the scope of the invention are chosen from hyperbranched polymers and dendrimers, and comprise at least one group of formula (I):

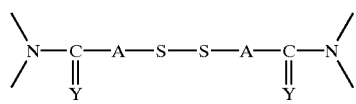

(I)

in which:
Y represents O or NH,
A represents a linear, branched or cyclic, saturated or unsaturated $C_1$–$C_{12}$ alkanediyl group, this group optionally being interrupted with one or more hetero atoms and/or substituted with a function chosen from:
amino (—$NH_2$) optionally in the form of a salt of an inorganic or organic acid,
acylamino (—NH—COR) in which R represents a linear, branched or cyclic, saturated or unsaturated $C_1$–$C_{10}$ alkyl group,
carboxylic acid (—COOH),
ester (—COOR) in which R represents a linear, branched or cyclic, saturated or unsaturated $C_1$–$C_{10}$ alkyl group.

Preferably, the compound according to the invention is chosen from hyperbranched polymers, and in particular polyethyleneimine, comprising at least one group of formula (I).

Preferably, Y represents an oxygen atom.

Preferably, the hetero atoms are chosen from oxygen and nitrogen (O and N).

Preferably, A is a methylene, ethylene, propylene, methylpropylene, ethylpropylene, tetramethylene, pentamethylene, hexamethylene, phenylene or phenyldiyl group.

Advantageously, A represents a radical corresponding to one of the formulae (a) to (d) below:

(a) —$CHR^1$—$CHR^2$—$CHR^3$—
(b) —$CHR'^1$—$CHR'^2$—$CHR'^3$—$CHR'^4$—

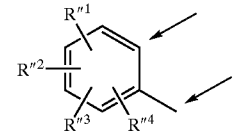

(c)

(d) —$(CHR'''^1)_k$—$(CHR'''^2)$—$CH(CO_2H)$—NH— in which
$R^1$, $R^2$, $R^3$, $R'^1$, $R'^2$, $R'^3$ and $R'^4$, $R'''^1$ and $R'''^2$, which may be identical or different, represent: a hydrogen atom; a linear, branched or cyclic, saturated or unsaturated $C_1$–$C_6$ alkyl radical; an amino (—$NH_2$) radical; a carboxylic acid (—COOH) radical; a $C_1$–$C_{10}$ alkylamino radical; a $C_1$–$C_{10}$ acylamino radical;
$R''^1$, $R''^2$, $R''^3$ and $R''^4$, which may be identical or different, represent: a hydrogen atom; a linear or branched, saturated or unsaturated $C_1$–$C_4$ alkyl radical, the arrows indicating the positions of the substitutions;
k is an integer, preferably 0 or 1.

Preferably, A is chosen from the following groups:
—$CH_2$—$CH(CO_2H)$—NH—; —$(CH_2)_2$—$(CH_3CONH)$CH—; —$(CH_2)_3$— and
—$CH_2$—$CH(NH$—CO—$CH_3)$—.

The compounds defined above can be obtained in particular by oxidation of the polymers described in patent application FR 97/04085, the content of which is incorporated by way of reference, and which are chosen from hyperbranched polymers and dendrimers, comprising functional groups corresponding to formula (II):

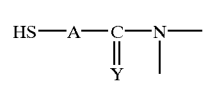

(II)

in which:
Y represents O or NH,
A represents a linear, branched or cyclic, saturated or unsaturated $C_1$–$C_{12}$ alkanediyl group, this group optionally being interrupted with one or more hetero atoms and/or substituted with a function chosen from amino, acylamino, carboxylic acid and ester.

The oxidation can be carried out by any known means, for example in air or using a common oxidizing agent such as hydrogen peroxide.

The oxidation step allows the formation of intramolecular and intermolecular disulphide bridges, starting with thiol functions, according to the scheme below:

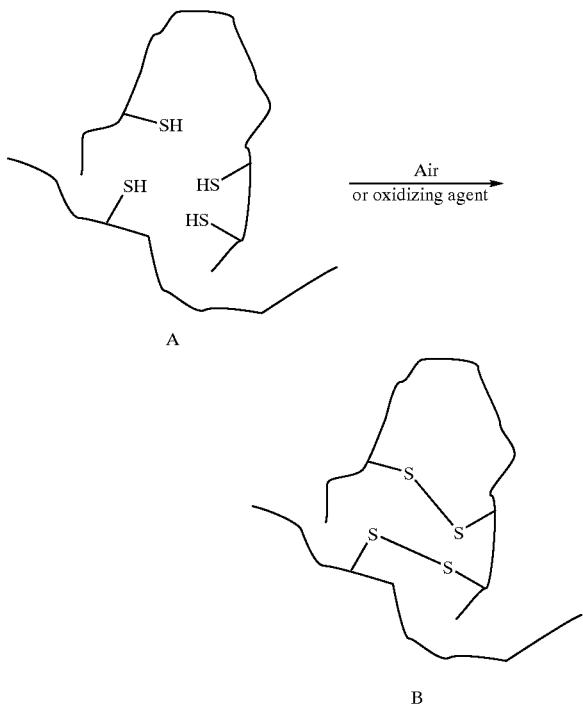

The formation of disulphide bridges brings about a "pseudo-crosslinking" of the starting compounds A, which is reflected in the formation of compounds B which make it possible to obtain films when they are deposited on a substrate.

The oxidation step is preferably carried out in the presence of water, for example in aqueous or aqueous-alcoholic medium.

After application on a substrate, it is thus possible to obtain films containing only one or more compounds B according to the invention and optionally starting compounds A that have not reacted, when the oxidation is only partially performed.

It has also been found that it is possible to incorporate, before oxidation, water-soluble or water-insoluble additives into the aqueous or aqueous-alcoholic medium while at the same time retaining the possibility of obtaining an adequate film.

Among the additives which can be incorporated, mention may be made of water-soluble dyes such as Rhodamine; water-soluble cosmetic or pharmaceutical active agents; water-insoluble products which have in particular optical properties such as phosphorescence or fluorescence; pigments; fillers; sunscreens; water-insoluble cosmetic or pharmaceutical active agents.

It has moreover been found that the solid additives, pigment particles or fillers, for example, were fully dispersed homogeneously in the film; they are fully enclosed in the structure of the film. There is no releaase of the particles, and the films are not tacky.

It is known that the properties of the films obtained depend on the oxidation conditions, in particular the concentration of starting thiol-containing polymer, the number of thiol functions in the said thiol-containing polymer, the molar mass of the said polymer and/or the pH of the aqueous/aqueous-alcoholic medium before oxidation.

Thus, the films can be prepared directly using an aqueous solution or an aqueous-alcoholic solution of thiol-containing polymer. During drying, the thiol functions will be oxidized to disulphides. It has been observed that, in this case, the films obtained may be visually non-uniform and may remain tacky.

When an aqueous or aqueous-alcoholic solution of thiol-containing polymer is oxidized chemically and when a film is prepared using this liquid oxidized solution, the film obtained after drying is generally very uniform, with a very uniform surface, glossy, transparent, colourless, highly adherent and may be brittle when it is desired to detach it. These films are not water-resistant.

It is thus possible to obtain a composition which can form films and which can be used in its native form, as a cosmetic or pharmaceutical composition, or incorporated into a composition, in particular a cosmetic or pharmaceutical composition, which can then comprise a cosmetically or pharmaceutically acceptable medium.

The said cosmetic or pharmaceutical composition can be in any form which is suitable for topical application, in particular in the form of aqueous or aqueous-alcoholic gels; in the form of water-in-oil, oil-in-water or multiple emulsions, of more or less thickened liquid consistency, such as a milk or cream; sprays or aerosol mousses; sticks or tubes; solutions or liquid dispersions.

A person skilled in the art knows how to prepare these compositions according to the usual methods, on the basis of his or her general knowledge.

In particular, these compositions can contain adjuvants usually used in the cosmetics or pharmaceuticals fields, such as oils, waxes or other common fatty substances; surfactants; moisturizers; emollients; sunscreens; hydrophilic or lipophilic active agents such as ceramides; free-radical scavengers; polymers; proteins; bactericides; sequestering agents; antidandruff agents; antioxidants; preserving agents; basifying or acidifying agents; fragrances; fillers; dyestuffs; cosmetic or pharmaceutical active agents. The amounts of these various adjuvants are those conventionally used in the fields under consideration and can readily be determined by a person skilled in the art.

Needless to say, a person skilled in the art will take care to select this or these optional additional adjuvant(s), and/or the amount thereof, such that the advantageous properties of the composition according to the invention are not, or are not substantially, adversely affected by the envisaged addition.

The compositions according to the invention are film-forming and can thus be used to form a film on a support, chosen in particular from the skin, mucous membranes, semi-mucous membranes, the nails and the hair of human beings.

The compositions according to the invention are, for example, lotions, milks or creams for skincare or haircare; make-up-removing creams, lotions or milks; foundation bases; antisun or after-sun lotions, milks or creams; artificial tanning lotions, milks or creams; shaving creams or foams; aftershave lotions; body hygiene compositions such as deodorant sticks or creams; shampoos; hair products for maintaining the hairstyle or for shaping the hair such as styling gels; hair-colouring products; lipsticks; mascaras or eyeliners which may be for treatment purposes; nail varnishes or nailcare products.

The invention is illustrated in greater detail in the examples which follow.

Examples 1 to 3 describe the preparation of the starting compounds of formula (II).

Examples 4 to 6 describe the preparation of the films according to the invention.

EXAMPLE 1
Branched Polyethyleneimine Polymer of Average Molecular Weight MW=25000 Containing 50 SH Functions on Average per Unit 12.28 g of water then, when the medium has become homogeneous again, 1.2 ml of γ-thiobutyrolactone (i.e. 50 molar equivalents calculated relative to the polymer) are added, at room temperature, to 12.28 grams of aqueous 56% solution of polyethyleneimine of average molecular weight MW=25000, sold by the company BASF under the name Lupasol HF, under inert atmosphere at room temperature. The medium, which is initially heterogeneous, rapidly becomes homogeneous (within about 30 minutes). After stirring for 24 hours, no more γ-thiobutyrolactone is detected in the medium.

This thus gives an aqueous solution of thiol-containing poly(ethyleneimine) of molar mass 30,108 containing on average 50 SH functions per polymer chain.

19.60 g of this solution are diluted with water qs 25 ml. This thus gives an aqueous solution containing 25 g/100 ml of thiol-containing polymer, i.e. 0.415 mol/l of thiol and 8.30 mmol/l of thiol-containing polymer. The pH of this solution is 10.65.

EXAMPLE 2
Branched Polyethyleneimine Polymer of Average Molecular Weight MW=25000 Containing 125 SH Functions on Average per Unit 22.43 g of water followed by 5.44 ml of γ-thiobutyrolactone (i.e. 125 molar equivalents calculated relative to the polymer) are added, at room temperature, to 22.43 grams of aqueous 56% solution of polyethyleneimine of average molecular weight MW=25000 sold by the company BASF under the name Lupasol HF, under inert atmosphere at room temperature. The medium, which is initially heterogeneous, rapidly becomes homogeneous (within about 30 minutes). After stirring for 24 hours, no more y-thiobutyrolactone is detected in the medium. This thus gives an aqueous solution of thiol-containing poly(ethyleneimine) of molar mass 37,770 containing on average 125 SH functions per polymer chain.

32.080 g of this solution are diluted with water qs 50 ml. This thus gives an aqueous solution containing 25 g/100 ml of thiol-containing polymer, i.e. 0.827 mol/l of thiol and 6.619 mmol/l of thiol-containing polymer. The pH of this solution is 9.96.

EXAMPLE 3
Branched Polyethyleneimine Polymer of Average Molecular Weight MW=2000 Containing 11.09 SH Functions on Average per Unit 12 ml of γ-thiobutyrolactone (i.e. 11.09 molar equivalents calculated relative to the polymer) are added, at room temperature, to 50 grams of aqueous 50% solution of polyethyleneimine of average molecular weight MW=2000 sold by the company BASF under the name Lupasol G35, under inert atmosphere at room temperature. The medium, which is initially heterogeneous, rapidly becomes homogeneous (within about 30 minutes). After stirring for 16 hours, no more γ-thiobutyrolactone is detected in the medium. This thus gives an aqueous solution of thiol-containing poly(ethyleneimine) of molar mass 3132.95 containing on average 11.09 SH functions per polymer chain.

This aqueous phase is diluted with water qs 100 ml. This thus gives an aqueous solution containing 39.16 g/100 ml of thiol-containing polymer, i.e. 1.386 mol/l of thiol. The pH of this solution is 10.15.

EXAMPLE 4
Preparation of Films from Thiol-containing Poly(ethyleneimine) according to Example 1 a) First Series

Starting with the solution containing 25 g/100 ml prepared in Example 1, various solutions are prepared by dilution with water and/or acidfiication with aqueous hydrochloric acid solution.

Their characteristics are as follows:

| Solution/film | pH | Concentration of thiol-containing polymer | Concentration of thiol (mol/l) |
|---|---|---|---|
| 1 | 10.65 | 8.303 mM 25 g/100 ml | 0.415 |
| 2 | 8.9 | 6.323 mM 19.05 g/100 ml | 0.316 |
| 3 | 7.9 | 5.641 mM 16.98 g/100 ml | 0.282 |
| 4 | 6.9 | 5.289 mM 15.923 g/100 ml | 0.264 |
| 5 | 5.7 | 4.942 mM 14.881 g/100 ml | 0.247 |

The films are prepared on 10 cm×10 cm glass plates. The depositions are made using a Baker Adjustable filmograph (Braive Instruments) and have a thickness of 150 microns.

They are left to dry in the ambient air, at 20° C., on a flat surface. The deposits are thus left to air-oxidize.

b) Second Series

Using the 25 g/100 ml solution prepared in Example 1, two other films are also prepared for which the polymer is totally oxidized with an aqueous 6% $H_2O_2$ solution. The liquid-oxidized solution is used to prepare films from deposits 150 microns thick on 10 cm×10 cm glass plates, using a Baker Adjustable filmograph (Braive Instruments). They are left to dry in the ambient air, at 20° C., on a flat surface.

Film 6:

An aqueous solution of oxidized polymer is prepared using 1 volume of thiol polymer solution prepared according to Example 1 at a concentration of 19.05 g/100 g (pH 8.96) diluted with 1 volume of water and oxidized with 1 equivalent of aqueous 6% hydrogen peroxide solution (the medium remains liquid after oxidation of the thiols to disulphide).

The film is prepared using this aqueous solution.

Film 7:

An aqueous solution of oxidized polymer is prepared using 1 volume of solution of thiol polymer prepared according to Example 1 at a concentration of 15.92 g/100 ml (pH 6.97) diluted with 0.2 volume of water and oxidized with 1 equivalent of aqueous 6% hydrogen peroxide solution. It is known, from preliminary tests, that the medium remains liquid for a few moments after adding the oxidizing agents, after which it gels.

The film is prepared using this aqueous solution before it has gelled.

c) Results of the Two Series 7 films are obtained, the characteristics of which are as follows, 24 hours after drying:

Film 1: tacky, shrunk, non-uniform surface

Films 2 to 5: tacky, non-uniform surface (presence of bubbles), do not change even after drying for several days Film 6: tacky, uniform surface. This film becomes dry and non-tacky after drying for 48 hours. It is then colourless, glossy, transparent and highly adherent Film 7: dry, non-tacky, glossy, very smooth surface, transparent, colourless and highly adherent.

Films 1 to 7 are water-washable.

EXAMPLE 5
Preparation of Films Starting with Thiol-containing Poly (ethyleneimine) According to Example 2 a) First Series

Starting with the solution containing 25 g/100 ml prepared in Example 2, various solutions are prepared by dilution with water and/or acidification with aqueous hydrochloric acid solution.

Their characteristics are as follows:

| Solution/film | pH | Concentration of thiol-containing polymer | Concentration of thiol (mol/l) |
|---|---|---|---|
| 8 | 8.9 | 10.52 mM<br>2.78 g/100 ml | 0.348 |
| 9 | 7.9 | 3.46 mM<br>13.06 g/100 ml | 0.432 |
| 10 | 5.0 | 4.583 mM<br>17.313 g/100 ml | 0.573 |

The films are prepared on 10 cm×10 cm glass plates. The depositions are made using a Baker Adjustable filmograph (Braive Instruments) and have a thickness of 250 microns.

They are left to dry in the ambient air, at 20° C., on a flat surface. The deposits are thus left to air-oxidize.

b) Second Series

Four other films are also prepared, for which the polymer is totally oxidized with 1 equivalent of an aqueous 6% $H_2O_2$ solution.

The oxidized solution which is still liquid, before its possible gelation, is used to prepare films starting with deposits 250 microns thick made on 10 cm×10 cm glass plates, using a Baker Adjustable filmograph (Braive Instruments).

They are left to dry in the ambient air, at 20° C., on a flat surface.

| Solution/film | pH before dilution | Concentration of thiol-containing polymer | Concentration of thiol (mol/l) |
|---|---|---|---|
| 11 | 7.9 | 2.36 mM<br>8.905 g/100 ml | 0.295 |
| 12 | 6.9 | 3.06 mM<br>11.56 g/100 ml | 0.382 |
| 13 | 5.8 | 3.96 mM<br>14.97 g/100 ml | 0.495 |
| 14 | 5.0 | 4.58 mM<br>17.31 g/100 ml | 0.573 | c) Results of the Two Series 7 films are obtained, the characteristics of which are as follows, after 24 hours of drying:

Film 8: dry, non-tacky, glossy, transparent, colourless and highly adherent

Film 9: tacky, shrunk, non-uniform surface (presence of bubbles), does not change even after drying for several days Film 10: tacky, slightly shrunk Film 11 to 14: dry, non-tacky, glossy, very smooth surface, transparent, colourless and highly adherent.

Films 8 to 14 are water-washable.

EXAMPLE 6
Preparation of Films Starting with Thiol-containing Poly (ethyleneimine) According to Example 3 a) First Series

Starting with the 39.16 g/100 ml solution prepared in Example 3, a solution at pH 7 is prepared by acidification with an aqueous hydrochloric acid solution. Its characteristics are as follows:

| Solution/film | pH | Concentration of thiol-containing polymer | Concentration of thiol (mol/l) |
|---|---|---|---|
| 15 | 7 | 82.668 mM<br>25.8994 g/100 ml | 0.9168 |

Starting with this solution, two aqueous or aqueous-alcoholic (water+absolute ethanol) samples are prepared containing:

Product A: blue-coloured pigment (FD&C Blue No. 1, Aluminium Lake, CI 42090:2)

Product B: red-coloured pigment (D&C Red No. 7, Calcium Lake)

according to the table below:

| Solution | Preparation | Concentration of thiol-containing polymer | Concentration of thiol (mol/l) | % of pigment* |
|---|---|---|---|---|
| 16 | 1 volume of sol. 15 + 0.8 volume of water | 45.927 mM<br>14.388 g/100 ml | 0.5093 | 2% product A |
| 17 | 1 volume of sol. 15 + 0.7 volume of EtOH | 48.628 mM<br>15.235 g/100 ml | 0.5393 | 1% product B |

*Calculated by weight relative to the weight of thiol-containing polymer

From preliminary tests, it is known that solutions 16 and 17, after addition of the oxidizing agent (1 equivalent of aqueous 6% $H_2O_2$ solution) remain liquid for a few moments before gelling.

Films are prepared using polymers undergoing oxidation, before gelation, i.e. during crosslinking (just after addition of 1 equivalent of aqueous 6% $H_2O_2$ solution, the oxidizing agent being added with vortex stirring).

The films are prepared on 10 cm×10 cm glass plates. The deposits are prepared using a Baker Adjustable filmograph (Braive Instruments) and have a thickness of 200 microns.

They are left to dry in the ambient air, at 20° C., on a flat surface.

After drying, two coloured films are obtained: film 16 is a transparent pale blue and film 17 is a transparent orange.

These two films have a very uniform surface, have a glossy appearance and appear uniform to the naked eye. They are not tacky. No pigment particles can be distinguished. These films are highly adherent and are water-washable.

b) Second Series

Starting with solution 15, two aqueous or aqueous-alcoholic (water+absolute ethanol) samples are prepared containing Rhodamine B (RN=[81-88-9]) according to the table below:

| Solution | Preparation | Concentration of thiol-containing polymer | Concentration of thiol (mol/l) | % of pigment* |
|---|---|---|---|---|
| 18 | 1 volume of sol. 15 + 0.7 volume of water | 48.628 mM 15.235 g/ 100 ml | 0.5393 | 0.1% |
| 19 | 1 volume of sol. 15 + 0.17 volume of EtOH + 0.41 volume of water | 52.45 mM 16.434 g/ 100 ml | 0.5817 | 0.028% |

*Calculated by weight relative to the weight of thiol-containing polymer

From preliminary tests, it is known that solutions 18 and 19, after addition of 1 equivalent of aqueous 6% $H_2O_2$ solution, remain liquid for a few moments before gelling.

Films are prepared using the solutions of polymers undergoing oxidation, before gelation, i.e. during crosslinking (just after addition of 1 equivalent of aqueous 6% $H_2O_2$ solution, the oxidizing agent being added with vortex stirring).

The films are prepared on 10 cm×10 cm glass plates. The depositions are made using a Baker Adjustable filmograph (Braive Instruments) and have a thickness of 200 microns.

They are left to dry in the ambient air, at 20° C., on a flat surface.

After drying, two transparent pale pink films are obtained. These two films have a very uniform surface, have a glossy appearance and appear uniform to the naked eye. They are not tacky. These films are highly adherent and are water-washable.

What is claimed is:

1. A film-forming composition comprising at least one compound chosen from hyperbranched polymers and dendrimers, wherein said hyperbranched polymers and dendrimers comprise at least one group of formula (I):

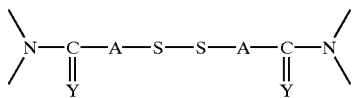

(I)

wherein:
Y is chosen from an oxygen atom and an NH group, and
A is chosen from linear, branched, and cyclic, saturated and unsaturated, $C_1$–$C_{12}$ alkanediyl groups, said groups being substituted with at least one group chosen from:
   amino;
   acylamino (—NH—CO—R) in which R is chosen from linear, branched, and cyclic, saturated and unsaturated, $C_1$–$C_{10}$ alkyl groups;
   carboxylic acid; and
   carboxylic acid esters (—COOR) in which R is chosen from linear, branched, and cyclic, saturated and unsaturated, $C_1$–$C_{10}$ alkyl groups,
   wherein A is optionally interrupted by at least one heteroatom.

2. A film-forming composition according to claim 1, wherein the alkanediyl group is interrupted by at least one heteroatom.

3. A film-forming composition according to claim 1, wherein the compound is a hyperbranched polymer.

4. A film-forming composition according to claim 1, wherein the compound is a dendrimer.

5. A film-forming composition according to claim 3, wherein the hyperbranched polymer is a polyethyleneimine comprising at least one group of formula (I).

6. A film-forming composition according to claim 1, wherein Y is an oxygen atom.

7. A film-forming composition according to claim 1, wherein A is a radical chosen from:
   (a) —$CHR^1$—$CHR^2$—$CHR^3$—
   (b) —$CHR'^1$—$CHR'^2$—$CHR'^3$—$CHR'^4$—

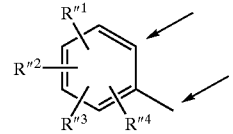

(c)

(d) —$(CHR'''^1)_k$—$(CHR'''^2)$—$CH(CO_2H)$—NH—
wherein
   $R^1$, $R^2$, $R^3$, $R'^1$, $R'^2$, $R'^3$ and $R'^4$, $R'''^1$ and $R'''^2$, which are identical or different, are independently chosen from:
      a hydrogen atom;
      linear, branched, and cyclic, saturated and unsaturated, $C_1$–$C_6$ alkyl radicals,
      an amino radical;
      a carboxylic acid radical;
      a $C_1$–$C_{10}$ alkylamino radical; and
      a $C_1$–$C_{10}$ acylamino radical;
   $R''^1$, $R''^2$, $R''^3$ and $R''^4$, which are identical or different, are independently chosen from:
      a hydrogen atom; and
      linear, branched, and cyclic, saturated and unsaturated, $C_1$–$C_4$ alkyl radicals, the arrows indicating the position of substitution;
   k is an integer chosen from 0 and 1.

8. A film-forming composition according to claim 1, wherein A is chosen from:
   (a) —$CH_2$—$CH(CO_2H)$—NH—;
   (b) —$(CH_2)_2$—$(CH_3CONH)CH$—; and
   (c) —$CH_2$—$CH(NH$—$CO$—$CH_3)$—.

9. A film-forming composition according to claim 1, further comprising a cosmetically or pharmaceutically acceptable medium.

10. A film-forming composition according to claim 9, wherein the cosmetically or pharmaceutically acceptable medium comprises at least one fatty substance.

11. A film-forming composition according to claim 10, wherein said at least one fatty substance is chosen from oils and waxes.

12. A film-forming composition according to claim 1, further comprising at least one adjuvant chosen from surfactants, moisturizers, emollients, sunscreens, hydrophilic active agents, lipophilic active agents, free-radical scavengers, polymers, proteins, bactericides, sequestering agents, antidandruff agents, antioxidants, preserving agents, basifying agents, acidifying agents, fragrances, fillers, dyestuffs, cosmetic active agents, and pharmaceutical active agents.

13. A film-forming composition according to claim 1 in a form chosen from an aqueous gel, an aqueous-alcoholic gel, a water-in-oil emulsion, an oil-in-water emulsion, a multiple emulsion, a cream, a milk, a spray mousse, an aerosol mousse, a stick, a tube, a solution, and a liquid dispersion.

14. A film-forming composition comprising at least one compound chosen from hyperbranched polymers and dendrimers, wherein said hyperbranched polymers and dendrimers comprise at least one group of formula (I):

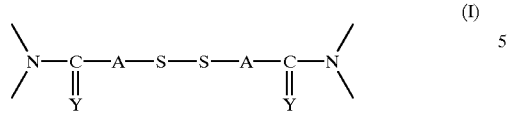

wherein:
Y is chosen from an oxygen atom and an NH group, and
A is chosen from linear, branched, and cyclic, saturated and unsaturated, $C_1$–$C_{12}$ alkanediyl groups, said groups being substituted with at least one group chosen from:
amino;
acylamino (—NH—CO—R) in which R is chosen from linear, branched, and cyclic, saturated and unsaturated, $C_1$–$C_{10}$ alkyl groups;
carboxylic acid; and
carboxylic acid esters (—COOR) in which R is chosen from linear, branched, and cyclic, saturated and unsaturated, $C_1$–$C_{10}$ alkyl groups,
wherein said film-forming composition is in a form chosen from a skincare or haircare lotion, milk, or cream; a make-up-removing lotion, milk, or cream; a foundation base; an antisun or after-sun lotion, milk, or cream; an artificial tanning lotion, milk, or cream; a shaving cream or foam; an aftershave lotion; a body hygiene composition; a shampoo; a hair product for maintaining the hairstyle or for shaping the hair; a hair-coloring product; a lipstick; a mascara or eyeliner; and a nail varnish or nailcare product.

15. A film-forming composition according to claim 14, wherein the body hygiene composition is a deodorant stick or cream.

16. A film forming composition according to claim 14, wherein the hair product for maintaining the hairstyle or shaping the hair is a styling gel.

17. A film-forming composition according to claim 14, wherein the mascara or eyeliner contains a pharmaceutical active agent.

18. A process for preparing a film-forming composition comprising at least one compound chosen from hyperbranched polymers and dendrimers, wherein said hyperbranched polymers and dendrimers comprise at least one group of formula (I):

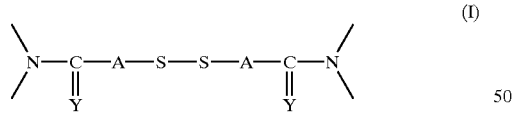

wherein:
Y is chosen from an oxygen atom and an NH group, and
A is chosen from linear, branched, and cyclic, saturated and unsaturated, $C_1$–$C_{12}$ alkanediyl groups, said groups being substituted with at least one group chosen from:
amino (—NH$_2$);
acylamino (—NH—CO—R) in which R is chosen from linear, branched, and cyclic, saturated and unsaturated, $C_1$–$C_{10}$ alkyl groups;
carboxylic acid (—COOH); and
carboxylic acid esters (—COOR) in which R is chosen from linear, branched, and cyclic, saturated and unsaturated, $C_1$–$C_{10}$ alkyl groups,
wherein A is optionally interrupted by at least one heteroatom, said process comprising oxidizing a composition comprising at least one polymer chosen from hyperbranched polymers and dendrimers, wherein said hyperbranched polymers and dendrimers comprise at least one group of formula (II):

wherein A and Y have the same meanings as in Formula (I).

19. A process according to claim 18, wherein A is interrupted by at least one heteroatom.

20. A process according to claim 18, wherein the oxidation is performed in air.

21. A process according to claim 18, wherein the oxidation is performed with an oxidizing agent.

22. A process according to claim 21, wherein the oxidizing agent is hydrogen peroxide.

23. A process according to claim 18, wherein the oxidation is performed in the presence of water.

24. A process according to claim 18, wherein the oxidation is performed in an aqueous medium.

25. A process according to claim 18, wherein the oxidation is performed in an aqueous-alcoholic medium.

26. A process according to claim 25, wherein additives are incorporated, before oxidation, into the aqueous-alcoholic medium.

27. A process according to claim 26, wherein the additives are chosen from dyes, cosmetic active agents, pharmaceutical active agents, fillers, sunscreens, and products having optical properties.

28. A process according to claim 27, wherein the dyes include Rhodamine.

29. A process according to claim 27, wherein the optical property is phosphorescence or fluorescence.

30. A process according to claim 18, wherein the film-forming composition further comprises a cosmetically or pharmaceutically acceptable medium.

31. A process for obtaining a film on a support, wherein a composition according to claim 1 is applied to the support.

32. A process for obtaining a film on a support, wherein:
a composition comprising a polymer chosen from hyperbranched polymers and dendrimers comprising at least one group of formula (II):

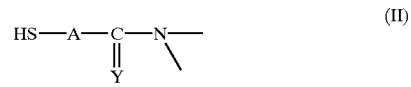

wherein:
Y is chosen from an oxygen atom and an NH group, and
A is chosen from linear, branched, and cyclic, saturated and unsaturated, $C_1$–$C_{12}$ alkanediyl groups, said groups being substituted with at least one group chosen from:
amino;
acylamino (—NH—CO—R) in which R is chosen from linear, branched, and cyclic, saturated and unsaturated, $C_1$–$C_{10}$ alkyl groups;
carboxylic acid; and
carboxylic acid esters (—COOR) in which R is chosen from linear, branched, and cyclic, saturated and unsaturated, $C_1$–$C_{10}$ alkyl groups, is applied to the support, and the composition is oxidized during or after its application to the support.

33. A process according to claim 31, wherein the support is chosen from the skin, mucous membranes, semi-mucous membranes, the nails, and the hair.

34. A process according to claim 32, wherein the support is chosen from the skin, mucous membranes, semi-mucous membranes, the nails, and the hair.

35. A process according to claim 24, wherein additives are incorporated before oxidation into the aqueous medium.

36. A film-forming composition comprising at least one compound chosen from hyperbranched polymers and dendrimers, wherein said hyperbranched polymers and dendrimers comprise at least one group of formula (I):

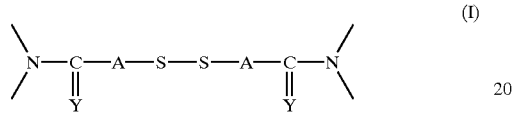

(I)

wherein:

Y is chosen from an oxygen atom and an NH group, and

A is chosen from linear, branched, and cyclic, saturated and unsaturated, $C_1$–$C_{12}$ alkanediyl groups, said groups being substituted with at least one group chosen from:

amino;

acylamino (—NH—CO—R) in which R is chosen from linear, branched, and cyclic, saturated and unsaturated, $C_1$–$C_{10}$ alkyl groups;

carboxylic acid; and carboxylic acid esters (—COOR) in which R is chosen from linear, branched, and cyclic, saturated and unsaturated, $C_1$–$C_{10}$ alkyl groups, wherein A is optionally interrupted by at least one heteroatom.

* * * * *